United States Patent [19]

Batt

[11] Patent Number: 5,006,555
[45] Date of Patent: Apr. 9, 1991

[54] ESTERS OF 2-ARYLMETHYL-1-NAPHTHOL DERIVATIVES AS 5-LIPOXYGENASE INHIBITORS

[75] Inventor: Douglas G. Batt, Wilmington, Del.

[73] Assignee: E. I. Du Pont de Nemours and Company, Wilmington, Del.

[21] Appl. No.: 466,601

[22] Filed: Jan. 17, 1990

[51] Int. Cl.$^5$ ............... A61K 31/22; C07C 69/03; C07D 213/55; C07D 333/24
[52] U.S. Cl. ................... 514/510; 514/277; 514/365; 514/428; 514/438; 514/546; 546/342; 548/204; 548/572; 549/79; 560/139
[58] Field of Search ............ 560/139; 546/342; 548/204, 572; 549/79; 514/277, 365, 428, 438, 546, 510

[56] References Cited

U.S. PATENT DOCUMENTS 4,374,855 2/1983 Resnick .................... 560/139 X
4,737,519 4/1988 Yamashita et al. ............ 514/510
4,833,164 5/1989 Batt ........................ 514/647

Primary Examiner—Jose G. Dees
Assistant Examiner—Vera C. Clarke

[57] ABSTRACT

There are provided novel esters of 2-arylmethyl-1-naphthol derivatives useful as anti-inflammatory agents. Also provided are pharmaceutical compositions containing these compounds and methods of using the compounds to treat inflammatory diseases in man.

36 Claims, No Drawings

ESTERS OF 2-ARYLMETHYL-1-NAPHTHOL DERIVATIVES AS 5-LIPOXYGENASE INHIBITORS

BACKGROUND OF THE INVENTION

1. Field of Invention

This invention relates to esters of 2-arylmethyl-1naphthol derivatives, pharmaceutical compositions containing them and methods of using them as 5-lipoxygenase inhibitors.

2. Background

The leukotrienes are oxidized polyunsaturated fatty acids which possess a multitude of biological activities. They are biosynthesized from arachidonic acid by the enzyme 5-lipoxygenase, which forms an unstable epoxide intermediate leukotriene A4 ($LTA_4$). Further enzymatic action on $LTA_4$ gives rise to two general classes of leukotrienes. The first class is represented by leukotriene $B_4$ ($LTB_4$). These compounds are chemotactic for inflammatory cells such as polymorphonuclear leukocytes, and cause degranulation and aggregation of inflammatory cells. They also increase vascular permeability, which leads to edema formation. A second class of leukotrienes, which includes $LTC_4$, $LTD_4$ and $LTE_4$, are formed from $LTA_4$ by the addition of glutathione to the epoxide, and by further metabolic alterations of the peptide portion. These compounds are the major components of slow-reacting substance of anaphylaxis, and have been implicated in immediate hypersensitivity reactions. They can cause, among other effects, the contraction of smooth muscle, increases in mucus secretion, and increased vascular permeability. Many literature reviews are available discussing the biosynthesis and biological activities of the leukotrienes. Examples are Ford-Hutchinson, *ISI Atlas of Science: Pharmacology* (1987) 1, 25; Parker, *Ann. Rev. Immunol.* (1987) 5, 65; Needleman et al., *Ann. Rev. Biochem.* (1986) 55, 69; Sirois, *Advan. Lipid Res.* (1985) 21, 79; and Kulkarni and Parale, *Drugs of Today* (1985) 21, 329.

Because of their many biological effects, the leukotrienes are involved in the pathology of numerous inflammatory diseases (Bray, *Agents Actions* (1986) 19, 87; and reviews cited above). Such diseases include, but are not limited to psoriasis, contact dermatitis, and other skin diseases (Greaves, in *Leukotrienes: Their Biological Significance.* P. J. Piper, ed; Raven (1986), p 175; Kragballe and Voorhees, *Acta Dermato-venereol.* (1985) suppl 120, 12), asthma and allergy (Lewis and Robin, *J. Allergy Clin. Immunol.* (1985) 76, 259), inflammatory bowel disease, ocular inflammation, arthritis, myocardial ischemia and circulatory shock (Lefer, *ISI Atlas of Science: Pharmacology* (1988) 2, 109). A therapeutic agent which effectively inhibits the biosynthesis of leukotrienes should be effective in the treatment of these and other inflammatory diseases where leukotrienes play a role (see, for example, Taylor and Clarke, *Trends Pharmacol Sci.* (1986) 7, 100; and Massicot et al., *Prostaglandins* (1986) 32, 481).

PRIOR ART

Several esters of 2-substituted 1-naphthol derivatives are reported in the literature as chemical entities: 1-benzoyl-2-benzylnaphthalene by Campbell et al. (*Proc. Royal Soc. Edinburgh* (1959-60) A65, 223); 1-acetoxy-2-benzyl-3,4-dimethylnaphthalene by Cromwell and Bambury (*J. Org. Chem.* (1961) 26, 997; *J. Am. Chem. Soc.* (1958) 80, 893); 1,4-diacetoxy-2-benzylnaphthalene by Miller and Lin (*J. Org. Chem.* (1979) 44, 887); 4-benzylthio-2-benzyl-1-acetoxynaphthalene by Buggle and O'Sullivan (*J. Chem. Soc. Perkin Trans* 1(1975), 572); 2-benzyl-3-methyl-6-(2-phenylethyl)-7-acetyl-1,8-Diacetoxynaphthalene by Takeuchi et al. (*Chem. Pharm. Bull.* (1980) 28, 3002); 2-benzyl-6,7-methoxy-1,3-diacetoxynaphthalene by Henin et al. (*Bull. Soc. Chim Fr.* (1976), 771); and 1,1'-diacetoxy-4,4'-diacetyldinaphthylmethane by Schonberg et al (*J. Org. Chem.* (1958) 23, 2025). A number of substituted 1-acetoxy-2-benzyl-3naphthoic acid derivatives have been reported by Kulkarni et al. (*J. Sci. Ind. Research (India)* (1961) 20 B, 30; *Indian J. Chem.* (1963) 1, 215; *Indian J. Chem.* (1964) 2, 235).

U.S. Pat. No. 4,737,519 issued to Yamashita et al. discloses substituted naphthalenes, of the structure:

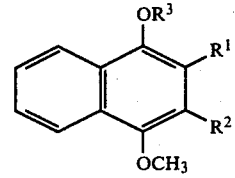

wherein $R^1$ and $R^2$ are hydrogen, alkyl, alkenyl, and optionally substituted phenyl; and $R^3$ is acetyl, amino acyl, substituted benzoyl, or other substituted acyl; subject to a number of provisos. These compounds are disclosed as useful in the treatment of deep-vein thrombosis and hypersecretion of mucus in the respiratory system. They are also reported to inhibit leukotriene production and/or 5-lipoxygenase.

Co-assigned U.S. Pat. No. 4,833,164 discloses 2-arylmethyl-1-naphthols of the structure:

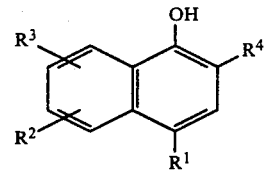

wherein $R^1$ is a variety of substituents, $R^2$ and $R^3$ are hydrogen, alkyl, or alkoxy, and $R^4$ is, among other groups, benzyl, substituted benzyl or heteroarylmethyl. These compounds are claimed as 5-lipoxygenase inhibitors and anti-inflammatory agents. Further disclosed in the co-assigned patent is 4-acetyl-2-benzyl-1-acetoxynaphthalene, which is used as an intermediate in the preparation of the corresponding free naphthol.

None of the above-described references disclose the compounds of the present invention useful as anti-inflammatory agents.

SUMMARY OF THE INVENTION

According to the present invention there are provided compounds having the formula:

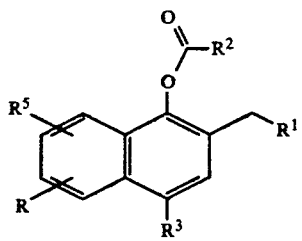

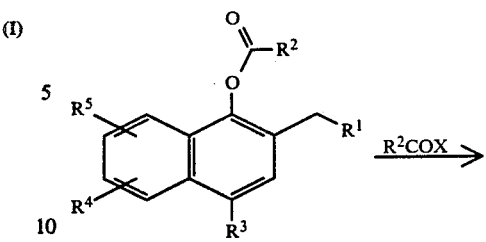

or a pharmaceutically acceptable salt thereof wherein:

$R^1$ is pyridyl, thienyl, N-methylpyrryl, thiazolyl, methylenedioxyphenyl, or phenyl optionally substituted with 1 to 3 substituents independently selected from the group consisting of F, Cl, Br, $C_1-C_4$ alkyl, $C_1-C_4$ alkoxy, $C_1-C_4$ acyloxy, $C_1-C_4$ alkylthio, $C_1-C_4$ alkylsulfonyl or $NR^6R^7$;

$R^2$ is $C_1-C_4$ alkyl, $C_1-C_4$ alkoxy, or $(CH2)_nR^8$ where n is 2–4;

$R^3$ hydrogen, $C_1-C_4$ alkyl, Br or Cl;

$R^4$ and $R^5$ independently are H, $C_1-C_4$ alkyl or $C_1-C_4$ alkoxy;

$R^6$ and $R^7$ independently are H or $C_1-C_4$ alkyl, or taken together are —(CH2)4—; $R^8$ is H, $COOR^9$ or $N(R^{10})_2$; and $R^9$ and $R^{10}$ independently are H or $C_1-C_4$ alkyl.

Also provided are pharmaceutical compositions containing compounds of Formula (I) and methods of using the 5-lipoxygenase inhibitor compounds of Formula (I) to treat inflammatory diseases in a mammal.

PREFERRED EMBODIMENTS

Preferred compounds are those compounds of Formula (I) wherein:

$R^1$ is phenyl substituted with one to three groups as specified above; and/or $R^2$ is methyl, ethyl or propyl; and/or $R^3$ is H or Cl; and/or $R^4$ and $R^5$ are H.

Specifically preferred compounds are:

(a) 1-acetoxy-2-phenylmethylnaphthalene;

(b) 1-acetoxy-2-(3,4-diaacetoxyphenylmethyl)naphthalene;

(c) 1-acetoxy-2-(3-methoxy-4-acetoxyphenylmethyl)-naphthalene;

(d) 1-acetoxy-2-(4-dimethylaminophenylmethyl)-naphthalene;

(e) 1-acetoxy-2-(2-ethoxyphenylmethyl)naphthalene; and (f) 1-acetoxy-2-(2,4,6-trimethoxyphenylmethyl)naphthalene.

DETAILED DESCRIPTION OF THE INVENTION

Synthesis

The preparation of the compounds of this invention is described below, and is demonstrated by Examples 1 through 4.

Compounds of Formula (I) can be prepared from compounds of Formula (II) by methods well known in the chemical literature. These methods involve treatment of the compound of Formula (II) with an activated carbonyl compound $R^2COX$, which can be, for example, a carboxylic acid chloride, a carboxylic acid bromide, a chloroformate ester, a carboxylic acid anhydride, a mixed anhydride or an activated compound prepared in situ. for instance by the reaction of a carboxylic acid with an activating reagent such as dicyclohexylcarbodiimide or oxalyl chloride. The molar ratio of the naphthol of Formula (II) to the activated carbonyl compound is between about 1:1 and 1:10, preferably between about 1:1 and 1:2. The reaction is usually performed in the presence of a base such as pyridine, triethylamine or 4-dimethylaminopyridine. The quantity of base used is usually at least that quantity which is sufficient to react with any acidic byproducts of the reaction and may also be present in large excess. A solvent is usually used for the reaction or alternatively the base (if a liquid) may serve as the solvent. Examples of suitable solvents include but are not limited to, dichloromethane, chloroform and tetrahydrofuran. The concentration of the reactants in the solvent is chosen to give a reasonable rate of reaction and a convenient reaction volume. The reaction is usually carried out at a temperature at which a reasonable rate of reaction is obtained, usually between about −78° C. and the boiling point of the reaction solvent. Preferred temperatures are between about 0° C. and room temperature.

An alternative method of preparing the compounds of Formula (I) is by treating the compound of Formula (II) with a base such as sodium hydride, potassium hydride, an alkali metal alkoxide or an organometallic compound such as an alkyllithium to form the anion, followed by treatment with an activated carbonyl compound as described above. Reaction solvents and conditions are also as described above, with the limitation that the solvent must be compatible with the base used to form the anion of the compound of Formula (II).

It will be recognized by one skilled in the art that certain substituents on $R^1$ may be incompatible with the reaction conditions used to form the ester. In these cases, appropriately protected compounds of Formula (II) may be used to prepare protected analogs of the corresponding compounds of Formula (I), after which known techniques may be used to remove the protecting groups. In particular, hydroxyl groups on $R^1$ must be protected, for example as benzyl ethers. A suitable method for deprotection, such as catalytic hydrogenolysis for example, may then be used to remove the protecting group after the ester has been formed. In cases where $R^1$ contains one or more acyloxy groups, the acyloxy compound may be prepared from the corresponding hydroxyl compound once the ester at the naphthalene 1-position has been prepared. If the acyloxy group on $R^1$ is the same as the acyloxy group at the naphthalene 1-position, the poly-ester may be prepared from the corresponding poly-hydroxyl compound using the same methods as described above, except that additional activated carbonyl compound may be required in order to react completely with all of the hydroxyl groups present.

Compounds of Formula (II) are known in the chemical literature. For example, these compounds and their preparations are disclosed in commonly assigned U.S. Pat. No. 4,833,164.

The preparation of the compounds of the invention is described in greater detail in Examples 1 through 4. In these examples, all temperatures are in degrees Celsius. All reactions are performed under an atmosphere of dry nitrogen. Concentration under reduced pressure is performed with a rotary evaporator using a water aspirator. Flash chromatography refers to the method of medium-pressure column chromatography described by Still, Kahn and Mitra (*J. Org. Chem.* (1978) 43, 2923). The composition of solvent mixtures used as chromatographic eluents are given in percentages by volume. Nuclear magnetic resonance (NMR) spectra were obtained at a field strength of 200 MHz; abbreviations for NMR data are as follows: s=singlet, d=doublet, t=triplet, q=quartet, m=multiplet, $CDCl_3$=deuterochloroform solvent, $DMSO-D_6$=deuterodimethyl sulfoxide solvent. Peak positions for NMR data are reported as parts per million downfield from the internal standard tetramethylsilane. Infrared spectra were obtained as thin films (neat) or as finely-ground suspensions in mineral oil (mull); data are reported as peak positions in inverse centimeters. Abbreviations for mass spectra are: EI=electron ionization, $CH_4$-$C_1$=methane chemical ionization: data are reported as the ratio of charge to mass of the parent ion, with relative intensities in parentheses. Parts and percentages are by weight unless otherwise indicated.

EXAMPLE 1

Preparation of 1-acetoxy-2-phenylmethylnaphthalene (Formula (I) : $R^1$ =phenyl, $R^2$ =$CH_3$, $R^3$, $R^4$, $R^5$=H).

A solution of acetic anhydride (3.27, 0.032 mol) in pyridine (50 mL) was stirred at 0°. 2-Phenylmethyl-1-naphthol (5.00 g, 0.021 mol) was added and the mixture was stirred while warming to room temperature. After 18 h, water was added and the mixture was extracted with ether. The ether phase was washed with dilute hydrochloric acid, then with water, then with brine and was dried over $MgSO_4$. Concentration afforded a brown oil which was flash chromatographed (5% ethyl acetate/hexane). The resulting oil crystallized on standing and was recrystallized (hexane) to provide the title compound (4.75 g, 82%) as white needles: mp 67°-69°; NMR ($CDCl_3$) 7.9-7.6 (m, 3H), 7.45 (m, 2H), 7.20 (m, 6H), 4.01 (s, 2H), 2.40 (s, 3H); IR (mull) 1760; Mass Spec (EI) 276 (9), 234 (100), 156 (20); Calcd. for $C_{19}H_{16}O_2$: C-82.57 H-5.84., Found: C-82.66 H-5.93

EXAMPLE 2

Preparation of 1-ethoxycarbonyloxy-2-phenylmethyl naphthalene (Formula (I) : $R^1$ =phenyl, $R^2$ =$OCH_2CH_3$. $R^3$, $R^4$, $R^5$=H).

A solution of 2-phenylmethyl-1-naphthol (5.00 g, 0.021 mol) and triethylamine (2.53 g, 0.025 mol) in dichloromethane (65 mL) was stirred at 0°. Ethyl chloroformate (2.73 g, 0.025 mol) was added and the mixture stirred for one hour at 0°, then for two hours at room temperature. Water was added and the mixture was extracted with dichloromethane. The organic phase was dried over $MgSO_4$ and concentrated. The residue was flash chromatographed (5% ethyl acetate/hexane) to provide the title compound (6.50 g, 100%) as a viscous oil: NMR ($CDCl_3$) 7.84 (t, J=8 Hz, 2H), 7.68 (d, J=7 Hz, IH), 7.50 (m, 2H), 7.25 (m, 6H), 4.30 (q, J=7 Hz, 2H), 4.IO (s, 2H), 1.36 (t, J=7 Hz, 3H); IR (neat) 1760; Mass Spec (EI) 306 (45), 262 (32), 234 (86), 215 (31); Calcd. for $C_{20}H_{18}O_3$: C-78.40 H-5.92; Found: C-78.49 H-6.06.

EXAMPLE 3

Preparation of 1-(3-carboxypropionyloxy)-2-phenylmethylnaphthalene (2-phenylmethyl-1-naphthol hydrogen succinate) (Formula (I) ; $R^1$=phenyl, $R^2$=$CH_2CH_2COOH$, $R^3$, $R^4$, $R^5$=H).

Sodium hydride (60% in mineral oil; 1.32 g, 0.33 mol) was washed free of mineral oil by stirring in hexane and decanting the solvent. Tetrahydrofuran (75 mL) was added and the suspension was stirred at 0°. A solution of 2-phenylmethyl1-naphthol (7.00 g, 0.030 mol) in tetrahydrofuran (100 mL) was added dropwise. After the mixture was stirred for two hours, a solution of succinic anhydride (3.30 g, 0.033 mol) in tetrahydrofuran (80 mL) was added dropwise. After stirring for one hour at 0°, 1 N hydrochloric acid was added slowly until the mixture was acidic. The tetrahydrofuran was removed on a rotary evaporator and the residue was extracted with ethyl acetate. The organic layer was washed with dilute hydrochloric acid, water and brine and was dried over $MgSO_4$. Concentration provided a yellow solid, which was recrystallized (1-chlorobutane) to provide the title compound (6.89 g, 69%) as white crystals: mp 139.5°-140.5°; NMR ($CDCl_3$) 7.79 (m, 2H), 7.66 (d, J=7 Hz, IH), 7.47 (m, 2H), 7.3-7.2 (m, 6H), 4.02 (s, 2H), 3.01 (t, J=6 Hz, 2H), 2.81 (t, J=6 Hz, 2H); IR (mull) 3200-2400, 1745, 1714; Calcd. for $C_{21}H_{18}O_4$: C-75.43 H-5.43; Found C-75.13 H-5.42.

EXAMPLE 4

Preparation of 1-(4-demethylamine-butyryloxy)-2-phenylmethylnaohthalene hydrochloride (Formula (I); $R^1$ =phenyl, $R^2$ =$CH_2CH_2CH_2N(CH_3)_2$·HCl. $R^3$, $R^4$, $R^5$=H).

4-Dimethylaminobutyric acid hydrochloride (2.0 g, 0.012 mol) was heated at reflux in oxalyl chloride (1.4 mL, 0.016 mol) until a clear solution resulted. The excess oxalyl chloride was removed by flushing the flask with nitrogen, the flask was cooled on ice and N,N-dimethylformamide (10 mL) was added. A solution of 2-phenylmethyl-1-naphthol (2.34 g, 0.010 mol) and triethylamine (2 mL) in dichloromethane (80 mL) was cooled on ice and treated with the acid chloride solution dropwise over 15 min. The mixture was stirred at room temperature for 20 min, then was filtered and the filtrate was concentrated. The residue was dissolved in dichloromethane (100 mL) and washed twice with 3% aqueous sodium hydroxide, then with water. The organic phase was dried over $Na_2SO_4$ and concentrated. The residue was dissolved in dichloromethane (5 mL) and ether (50 mL) and treated with gaseous HCl. The precipitate was triturated with ether and collected by filtration to give the title product as a white solid (65%): mp 131°–134°; NMR (DMSO-D6) 10.6 (broad s, IH), 8.0-7.2 (11H), 4.0 (s, 2H), 3.2-3.0 (m, 4H), 2.8 (s, 6H), 2.2-2.0 (m, 2H); Calcd. for $C_{23}H_{26}ClNO_2 \cdot (H_2O)_{0.75}$: C-69.50 H-6.97 N-3.52 Cl-8.92; Found: C-69.44 H-7.02 N-3.52 Cl-8.95.

Additional compounds which were or may be prepared using the procedures of Examples 1-4 are shown in Table 1.

Utility

The compounds of this invention have been shown to inhibit 5-lipoxygenase in an in vitro test system using rat basophilic leukemia (RBL-1) cells as the source of the enzyme. The test method is a modification of the procedure developed by Jakschik et al. (*Prostaglandins* (1978) 16. 733; *Biochem. Biophys. Res. Commun.* (1980) 95. 103; Biochem. Biophys, Res. Commun. (1981) 102 624).

The 10,000 xg supernatant from homogenized RBL-1 cells was incubated with test compound in a pH 7.0 phosphate buffer for about five minutes. $^{14}C$-arachidonic acid was added to initiate the reaction, which was allowed to continue at 37° for two minutes. The reaction was stopped by freezing in a dry ice/ethanol slurry and the 5-lipoxygenase products were separated from the substrate on silica gel columns. The amount of individual lipoxygenase products produced was determined and the percent inhibition calculated.

TABLE 1

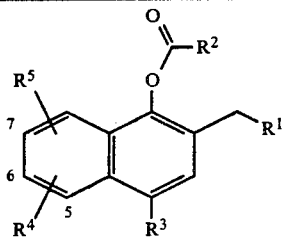

| Ex. No. | $R^1$ | $R^2$ | $R^3$ | $R^4$ or $R^5$ | m.p. (°C.) |
|---|---|---|---|---|---|
| 1 | $C_6H_5$ | $CH_3$ | H | H | 67–69 |
| 2 | $C_6H_5$ | $OCH_2CH_3$ | H | H | (oil)[a] |
| 3 | $C_6H_5$ | $CH_2CH_2COOH$ | H | H | 139.5–140.5 |
| 4 | $C_6H_5$ | $(CH_2)_3N(CH_3)_2HCl$ | H | H | 131–134 |
| 5 | $C_6H_5$ | $CH_2CH_3$ | H | H | (oil)[b] |
| 6 | $C_6H_5$ | $CH_2CH_2COOCH_3$ | H | H | (oil)[c] |
| 7 | $2-FC_6H_4$ | $CH_3$ | H | H | 77–79 |
| 8 | $3-FC_6H_4$ | $CH_3$ | H | H | 74–76 |
| 9 | $4-FC_6H_4$ | $CH_3$ | H | H | 89–91 |
| 10 | $4-CH_3OC_6H_4$ | $CH_3$ | H | H | 76–78 |
| 11 | $3,4-(CH_3O)_2C_6H_3$ | $CH_3$ | H | H | 88–89 |
| 12 | $3,4-(CH_3COO)_2C_6H_3$ | $CH_3$ | H | H | 113–115 |
| 13 | $3-CH_3O-4-CH_3COOC_6H_3$ | $CH_3$ | H | H | 74–78 |
| 14 | $3,4-(OCH_2O)C_6H_3$ | $CH_3$ | H | H | 125–126 |
| 15 | $4-N(CH_3)_2C_6H_4$ | $CH_3$ | H | H | 92–93 |
| 16 | $2-(N-CH_3O$-pyrryl) | $CH_3$ | H | H | 90–92 |
| 17 | 2-thienyl | $CH_3$ | H | H | 70–71 |
| 18 | 2-thiazolyl | $CH_3$ | H | H | 68–69 |
| 19 | $C_6H_5$ | $CH_3$ | 4-Cl | H | |
| 20 | $C_6H_5$ | $CH_3$ | $4-CH_3$ | H | |
| 21 | $C_6H_5$ | $CH_2CH_2CH_3$ | 4-Br | H | |
| 22 | $C_6H_5$ | $CH_3$ | H | $5-CH_3O$ | |
| 23 | $4-N(CH_2)_4C_6H_4$ | $CH_3$ | H | $6,7-(CH_3O)_2$ | |
| 24 | $3,4-Cl_2C_6H_3$ | $CH_3$ | H | $5,7-(CH_3)_2$ | |
| 25 | 3-pyridyl | $CH_3$ | H | H | |
| 26 | $3-BrC_6H_4$ | $CH_3$ | H | H | |
| 27 | $4-(CH_3)_2CHOC_6H_4$ | $CH_3$ | H | H | |
| 28 | $4-CH_3(CH_2)_3OC_6H_4$ | $CH_3$ | H | H | |
| 29 | $4-CH_3(CH_2)_3C_6H_4$ | $CH_3$ | H | H | |
| 30 | $3-CH_3(CH_2)_2C_6H_4$ | $CH_3$ | H | H | |
| 31 | $4-CH_3SO_2C_6H_4$ | $CH_3$ | H | H | |
| 32 | $4-C_2H_5SO_2C_6H_4$ | $CH_3(CH_2)_3$ | H | H | |
| 33 | $4-CH_3(CH_2)_3SO_2C_6H_4$ | $CH_3$ | H | H | |
| 34 | $C_6H_5$ | $CH_3$ | H | $5-CH_3(CH_2)_3O$ | |
| 35 | $C_6H_5$ | $CH_3$ | H | $6-CH_3(CH_2)_3$ | |
| 36 | $2-C_2H_5C_6H_4$ | $CH_3$ | H | H | |
| 37 | $2,4,6-(CH_3)_3C_6H_2$ | $CH_3$ | H | H | |

Footnotes for Table 1
[a]NMR (CDCl3) 7.84 (t, J = 8 Hz, 2H), 7.68 (d, J = 7 Hz, 1H), 7.50 (m, 2H), 7.25 (m, 6H), 4.30 (q, J = 7 Hz, 2H), 4.10 (s, 2H), 1.36 (t, J = 7 Hz, 3H); IR (neat) 1760; Mass Spec (EI) 306 (45), 262 (32); 234 (86), 215 (31); Calcd. for $C_{20}H_{18}O_3$: C-78.40, H-5.92; Found: C-78.49 H-6.06.
[b]NMR (CDCl3) 7.9–7.6 (3H), 7.55–7.4 (2H), 7.3–7.15 (6H), 4.04 (s, 2H), 2.75 (q, J = 7.5 Hz, 2H), 1.35 (t, J = 7.5 Hz, 3H); IR (neat) 1760; Mass Spec ($CH_4$—CI) 291(45), 235(100); Calcd. for $C_{20}H_{18}O_2$: C-82.73, H-6.25; Found C-82.45, H-6.26.
[c]NMR (CDCl3) 7.79 (m, 2H), 7.66 (d, J = 7 Hz, 1H), 7.42 (m, 2H), 7.3–7.1 (m, 6H), 4.03 (s, 2H), 3.67 (s, 3H), 3.03 (t, J = 6 Hz, 2H), 2.76 (t, J = 6 Hz, 2H); IR (neat) 1737; Mass Spec (EI). 348(6),317(3), 234(100).

The enzyme 5-lipoxygenase catalyzes the first reaction in the biosynthesis of the potent biological mediators, the leukotriens ($LTB_4$, $LTC_4$, $LTD_4$, $LTE_4$) from arachidonic acid. Collectively $LTC_4$, $LTD_4$, and $LTE_4$ are the materials which used to be known as slow reacting substance of anaphylaxis (SRS-A) before they were chemically characterized as leukotrienes. $LTC_4$ and $LTD_4$ are extremely potent mediators of anaphylaxis and seem to be particularly effective at reducing the air flow in peripheral airways. In animal models, reduction of the synthesis of SRS-A leads to a reduction in the symptoms following an allergic challenge. $LTB_4$ is a potent leukocyte chemotactic factor and aggregating agent. Polymorphonuclear leukocytes (PMN) are particularly sensitive to activation by $LTB_4$. Reduction of the synthesis of $LTB_4$ by blocking 5-lipoxygenase should reduce the influx of PMN to an inflamed site-either an arthritic joint or a psoriatic lesion. Elevated levels of $LTB_4$ have been found in both the synovial fluid of rheumatoid patients and in the plaque area of psoriasis patients. Thus a 5-lipoxygenase inhibitor, by reducing the production of these potent biological mediators, is useful for the treatment of inflammation, chronic obstructive lung diseases such as asthma and bronchitis, and skin diseases such as psoriasis.

5-Lipoxygenase inhibitory activities for selected compounds of this invention are shown in Table 1.

TABLE I

| Example | 5-lipoxygenase $IC_{50}$, $\mu M$ |
|---------|------------------------------------|
| 1  | 0.14  |
| 2  | 1.2   |
| 3  | 0.53  |
| 4  | 0.52  |
| 8  | 0.062 |
| 10 | 0.090 |
| 11 | 0.58  |
| 12 | 1.6   |
| 14 | 0.19  |
| 15 | 0.81  |
| 17 | 0.070 |

The compounds of this invention have been found to inhibit arachidonic acid-induced ear edema. This assay indicates a specific use in the treatment of skin diseases such as psoriasis. This assay also implies a reduction in leukotrienes caused by the compounds of the invention and indicates the use of these compounds in other diseases where the production of leukotrienes is involved in the pathological process. The assay is a modification of the procedure described by Young et al. (J. Invest. Dermatol. (1983) 80. 48).

Arachidonic acid (1 mg) was applied as an acetone solution to the inner surface of the pinna of CF1 mice. Test compound dissolved in acetone was applied to the ear just prior to the arachidonic acid challenge. One hour after challenge, 6 mm disks were removed from the ear with a biopsy punch and the weight determined. The results were determined as a percent inhibition of the swelling which occurred in the absence of the test compound.

Activities for selected compounds of the invention in the arachidonic acid ear edema assay are shown in Table II.

TABLE II

| Example | Arachidonic Acid Ear Edema % Inhibition at 100 $\mu g$/ear |
|---------|------------------------------------------------------------|
| 1  | 66 |
| 2  | 50 |
| 4  | 44 |
| 7  | 72 |
| 10 | 53 |
| 12 | 35 |
| 15 | 49 |
| 17 | 52 |

Significant inhibitory activity is considered to be greater than 30% inhibition. 50% and above is considered to be good to excellent activity.

Pharmaceutical Compositions

The compounds of the invention can be administered to treat inflammation, including but not limited to, rheumatoid arthritis, osteoarthritis, psoriasis, contact dermatitis, allergy, asthma and bronchitis, by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent and its mode and route of administration; age, health and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50 and preferably 1 to 25 milligrams per kilogram per day given in divided doses 1 to 6 times a day or in sustained release form is effective to obtain desired results.

Compositions (dosage forms) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets and powders, or in liquid dosage forms, such as elixirs, syrups and suspensions. It can also be administered parenterally in sterile liquid dosage forms. It can also be administered by inhalation in the form of a nasal spray or lung inhaler. It can also be administered topically as an ointment, cream, gel, paste, lotion, spray, aerosol, liposome or patch. Dosage forms used to administer the active ingredient usually contain suitable carriers, diluents, preservatives or other excipients, as described in Reminoton's Pharmaceutical Sciences, A. Osol (17th Edition, 1985), a standard reference text in the field.

Gelatin capsules contain the active ingredient and powdered carriers, such as lactose, sucrose, mannitol, starch, cellulose derivatives, magnesium stearate, stearic acid and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols such as propylene glycol or polyethylene glycols are suitable carriers for parenteral solutions. Solutions for parenteral administration contain the active ingredient, suitable stabilizing agents and if necessary, buffer substances. Anti-oxidizing agents such as sodium bisulfite, sodium sulfite or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben and chlorobutanol.

The topical ointments, creams, gels and pastes can contain diluents such as waxes, paraffins, starch, polyethylene glycol, silicones, bentonites, silicic acid, animal and vegetable fats, talc and zinc oxide or mixtures of these or other diluents. Topical solutions and emulsions can, for example, contain the customary diluents (with the exclusion of solvents having a molecular weight below 200 except in the presence of a surface-active agent), such as solvents, dissolving agents and emulsifiers; specific examples are water, ethanol, isopropanol, ethyl carbonate, benzyl alcohol, propylene glycol, oils, glycerol and fatty acid esters of sorbitol or mixtures thereof. Compositions for topical dosing may also contain preservatives or anti-oxidizing agents.

Powders and sprays can contain the usual diluents, such as lactose, talc, silicic acid, aluminum hydroxide, calcium silicate and polyamide powders or mixtures of these materials. Aerosol sprays can contain the usual propellants. Liposomes can be made from such materials as animal or vegetable fats which will form lipid bilayers in which the active ingredient can be incorporated.

Patches can be made of a matrix such as polyacrylamide, and a semipermeable membrane made from a suitable polymer to control the rate at which the material is delivered to the skin.

Useful pharmaceutical compositions for administration of the compounds of this invention can be illustrated as follows:

CAPSULES: A large number of unit capsules are prepared by filling standard two-piece hard gelatin capsules each with 50 mg of powdered active ingredient, 175 mg of lactose, 24 mg of talc and 6 mg of magnesium stearate.

SOFT GELATIN CAPSULES: A mixture of active ingredient in soybean oil is prepared and injected by means of a positive displacement pump into gelatin to form soft gelatin capsules containing 50 mg of the active ingredient. The capsules are washed in petroleum ether and dried.

TABLETS: A large number of tablets are prepared by conventional procedures so that the dosage unit is 50 mg of active ingredient, 6 mg of magnesium stearate, 70 mg of microcrystalline cellulose, 11 mg of cornstarch and 225 mg of lactose. Appropriate coatings may be applied to increase palatability or delay absorption.

SUSPENSION: An aqueous suspension is prepared for oral administration so that each 5 mL contain 25 mg of finely divided active ingredient, 200 mg of sodium carboxymethyl cellulose, 5 mg of sodium benzoate, 1.0 g of sorbitol solution, U.S.P. and 0.025 mg of vanillin.

INJECTABLE: A parenteral composition suitable for administration by injection is prepared by stirring 1.5% by weight of active ingredient in 10% by volume propylene glycol and water. The solution is sterilized by commonly used techniques.

NASAL SPRAY: An aqueous solution is prepared such that each 1 mL contains 10 mg of active ingredient, 1.8 mg methylparaben, 0.2 mg propyl-paraben and 10 mg methylcellulose. The solution is dispensed into 1 mL vials.

LUNG INHALER: A homogeneous mixture of the active ingredient in polysorbate BO is prepared such that the final concentration of the active ingredient will be 10 mg per container and the final concentration of polysorbate BO in the container will be 1% by weight. The mixture is dispensed into each can, the valves are crimped onto the can and the required amount of dichlorotetrafluoroethane is added under pressure.

OINTMENT: The active ingredient is added to a mixture of 48% by weight white petrolatum, 10% liquid petrolatum, 8% glycerol monostearate, 3% isopropyl myristate and 20% lanolin at 70° C. After thorough mixing, a warm solution of methyl and propyl parabens in water containing sodium acetone bisulfite is added such that the final concentrations of each paraben is 0.15%, of water is 8%, and of sodium acetone bisulfite is 0.5%. The mixture is stirred until it has reached room temperature.

What is claimed is:

1. A compound having the formula:

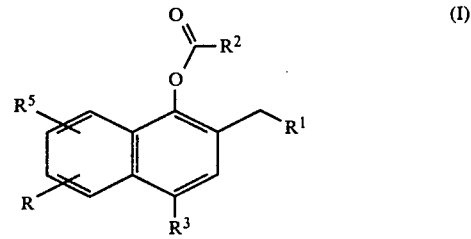

or a pharmaceutically acceptable salt thereof wherein:
$R^1$ is pyridyl thienyl N-methylpyrryl, thiazolyl, methylenedioxyphenyl, phenyl, or phenyl substituted with 1 to 3 substituents independently selected from the group consisting of F, Cl, Br, $C_1$-$C_4$ alkyl, $C_1$-$C_4$ alkoxy, $C_1$-$C_4$ acyloxy, $C_1$-$C_4$ alkylthio, $C_1$-$C_4$ alkylsulfonyl $NR^6R^7$;
$R^2$ is $C_1$-$C_4$ alkyl, $C_1$-$C_4$ alkoxy, or $(CH_2)_nR^8$ where n is 2–4;
$R^3$ hydrogen, $C_1$-$C_4$ alkyl, Br or Cl;
$R^4$ and $R^5$ independently are H, $C_1$-$C_4$ alkyl or $C_1$-$C_4$ alkoxy;
$R^6$ and $R^7$ independently are H or $C_1$-$C_4$ alkyl, or taken together are -$(CH_2)_4$-;
$R^8$ is H, $COOR^9$ or $N(R^{10})_2$; and
$R^9$ and $R^{10}$ independently are H or $C_1$-$C_4$ alkyl.

2. A compound of claim 1 wherein $R^1$ is phenyl optionally substituted with one to three groups independently selected from the group consisting of: F, Cl, Br, $C_1$-$C_4$ alkyl, $C_1$-$C_4$ alkoxy, $C_1$-$C_4$ acyloxy, $C_1$-$C_4$ alkylthio, $C_1$-$C_4$ alkylsulfonyl and $NR^6R^7$.

3. A compound of claim 1 wherein $R^2$ is methyl, ethyl or propyl.

4. A compound of claim 1 wherein $R^3$ is H or Cl.

5. A compound of claim 1 wherein $R^4$ and $R^5$ are H.

6. A compound of claim 1 wherein:

$R^1$ is phenyl or phenxy substituted with one to three groups independently selected from the group consisting of: F, Cl, Br, $C_1$-$C_4$ alkyl, $C_1$-$C_4$ alkoxy acyloxy, $C_1$-$C_4$ alkylthio, $C_1$-$C_4$ alkylsulfonyl and $NR^6R^7$;

$R^2$ is methyl, ethyl or propyl;

$R^3$ is H or Cl; and $R^4$ and $R^5$ are H.

7. The compound of claim 6 which is 1-acetoxy-2-phenylmethylnaphthalene.

8. The compound of claim 6 which is 1-acetoxy-2-(3,4-diaacetoxyphenylmethyl)naphthalene.

9. The compound of claim 6 which is 1-acetoxy-2-(3-methoxy-4-acetoxyphenylmethyl)naphthalene.

10. The compound of claim 6 which is 1-acetoxy-2-(4-dimethylaminophenylmethyl)naphthalene.

11. The compound of claim 6 which is 1-acetoxy-2-(2-ethoxyphenylmethyl)naphthalene.

12. The compound of claim 6 which is 1-acetoxy-2-(2,4,6-trimethoxyphenylmethyl)naphthalene.

13. An anti-inflammatory pharmaceutical composition comprising a pharmaceutically acceptable carrier and an anti-inflammatory effective amount of a compound of claim 1.

14. An anti-inflammatory pharmaceutical composition comprising a pharmaceutically acceptable carrier and an anti-inflammatory effective amount of a compound of claim 2.

15. An anti-inflammatory pharmaceutical composition comprising a pharmaceutically acceptable carrier and an anti-inflammatory effective amount of a compound of claim 3.

16. An anti-inflammatory pharmaceutical composition comprising a pharmaceutically acceptable carrier and an anti-inflammatory effective amount of a compound of claim 4.

17. An anti-inflammatory pharmaceutical composition comprising a pharmaceutically acceptable carrier and an anti-inflammatory effective amount of a compound of claim 5.

18. An anti-inflammatory pharmaceutical composition comprising a pharmaceutically acceptable carrier and an anti-inflammatory effective amount of a compound of claim 6.

19. An anti-inflammatory pharmaceutical composition comprising a pharmaceutically acceptable carrier and an anti-inflammatory effective amount of the compound of claim 7.

20. An anti-inflammatory pharmaceutical composition comprising a pharmaceutically acceptable carrier and an anti-inflammatory effective amount of the compound of claim 8.

21. An anti-inflammatory pharmaceutical composition comprising a pharmaceutically acceptable carrier and an anti-inflammatory effective amount of the compound of claim 9.

22. An anti-inflammatory pharmaceutical composition comprising a pharmaceutically acceptable carrier and an anti-inflammatory effective amount of the compound of claim 10.

23. An anti-inflammatory pharmaceutical composition comprising a pharmaceutically acceptable carrier and an anti-inflammatory effective amount of the compound of claim 11.

24. An anti-inflammatory pharmaceutical composition comprising a pharmaceutically acceptable carrier and an anti-inflammatory effective amount of the compound of claim 12.

25. A method of treating an inflammatory disease in a mammal comprising administering to the mammal an anti-inflammatory effective amount of a compound of claim 1.

26. A method of treating an inflammatory disease in a mammal comprising administering to the mammal an anti-inflammatory effective amount of a compound of claim 2.

27. A method of treating an inflammatory disease in a mammal comprising administering to the mammal an anti-inflammatory effective amount of a compound of claim 3.

28. A method of treating an inflammatory disease in a mammal comprising administering to the mammal an anti-inflammatory effective amount of a compound of claim 4.

29. A method of treating an inflammatory disease in a mammal comprising administering to the mammal an anti-inflammatory effective amount of a compound of claim 5.

30. A method of treating an inflammatory disease in a mammal comprising administering to the mammal an anti-inflammatory effective amount of a compound of claim 6.

31. A method of treating an inflammatory disease in a mammal comprising administering to the mammal an anti-inflammatory effective amount of the compound of claim 7.

32. A method of treating an inflammatory disease in a mammal comprising administering to the mammal an anti-inflammatory effective amount of the compound of claim 8.

33. A method of treating an inflammatory disease in a mammal comprising administering to the mammal an anti-inflammatory effective amount of the compound of claim 9.

34. A method of treating an inflammatory disease in a mammal comprising administering to the mammal an anti-inflammatory effective amount of the compound of claim 10.

35. A method of treating an inflammatory disease in a mammal comprising administering to the mammal an anti-inflammatory effective amount of the compound of claim 11.

36. A method of treating an inflammatory disease in a mammal comprising administering to the mammal an anti-inflammatory effective amount of the compound of claim 12.

* * * * *